United States Patent [19]

Takeichi et al.

[11] 4,370,985
[45] Feb. 1, 1983

[54] MEDICAL MEASURING APPARATUS

[75] Inventors: Hitoshi Takeichi, Kawasaki; Hiroshi Furuhata, Kasukabe; Ryoichi Kanno, Funabashi, all of Japan; Kuniyasu Kodaira, c/o Hayashi Denki Company Ltd., 2-7-11, Arima, Takatsu-ku, Kawasaki-shi, Kanagawa-ken, Japan; Mitio Ohno; Hirozi Matumoto, both of Kawasaki, Japan

[73] Assignee: Kuniyasu Kodaira, Japan

[21] Appl. No.: 142,098

[22] Filed: Apr. 21, 1980

[30] Foreign Application Priority Data

Apr. 26, 1979 [JP] Japan .................................. 54/51840

[51] Int. Cl.³ ............................................. A61B 10/00
[52] U.S. Cl. .................................... 128/663; 73/861.25
[58] Field of Search ............................... 128/660–663; 73/861.25, 861.27–861.29, 227

[56] References Cited

U.S. PATENT DOCUMENTS

| | | | |
|---|---|---|---|
| 3,498,290 | 3/1970 | Shaw et al. | 73/227 X |
| 3,974,692 | 8/1976 | Hassler | 128/663 |
| 3,987,673 | 10/1976 | Hansen | 73/861.25 |
| 4,095,597 | 6/1978 | Hassler | 128/663 |
| 4,122,713 | 10/1978 | Stasy et al. | 128/663 |
| 4,217,909 | 8/1980 | Papodofrangokis et al. | 128/663 |

Primary Examiner—Kyle L. Howell
Assistant Examiner—Francis J. Jaworski

[57] ABSTRACT

A medical measuring apparatus having an ultrasonic wave probe adapted to make contact with a body surface and two cathode ray tubes. The probe functions to deliver outputs associated with a blood flow speed and a blood vessel diameter deviation output. An output representing an amount of blood flow is formed on the basis of both the outputs associated with the blood flow speed and the blood vessel diameter deviation output. The output representing the amount of blood flow is displayed on the first cathode ray tube, while the blood vessel diameter deviation output and the pulse output having the width corresponding to the blood vessel diameter are displayed on the second cathode ray tube.

6 Claims, 35 Drawing Figures

MEDICAL MEASURING APPARATUS

BACKGROUND OF THE INVENTION

1. Field of the Invention

This invention relates to ultrasonic medical measuring apparatus which can observe various functions of blood flow and blood vessel action at a body surface.

2. Description of the Prior Art

It is possible to know a cerebral circulation characteristic (cerebral blood vessel characteristic) which can effectively predict a cerebral blood vessel defect such as cerebral arteriosclerosis or the like by making the blood vessel characteristics of carotid artery clear. In order to make the blood vessel characteristics clear, it is necessary to know not only the blood pressure and blood flow speed of the carotid artery at a position to be measured but also the blood vessel diameter and amount of blood flow.

SUMMARY OF THE INVENTION

An object of the invention, therefore, is to provide a medical measuring apparatus which can observe the above mentioned various kinds of data by electric wave forms.

A feature of the invention is the provision of a medical measuring apparatus comprising an ultrasonic wave probe for measuring an amount of blood flow and delivering outputs associated with a blood flow speed and a blood vessel diameter deviation output corresponding to a blood vessel diameter deviation, a first cathode ray tube for displaying an output representing an amount of blood flow formed on the basis of both the output associated with the blood flow speed and the blood vessel diameter deviation output, and a second cathode ray tube for displaying the blood vessel diameter deviation output and also displaying a pulse output having a width corresponding to the blood vessel diameter.

Further objects and features of the invention will be fully understood from the following detailed description with reference to the accompanying drawings.

DETAILED DESCRIPTION OF THE PREFERRED EMBODIMENTS

Figure 1:
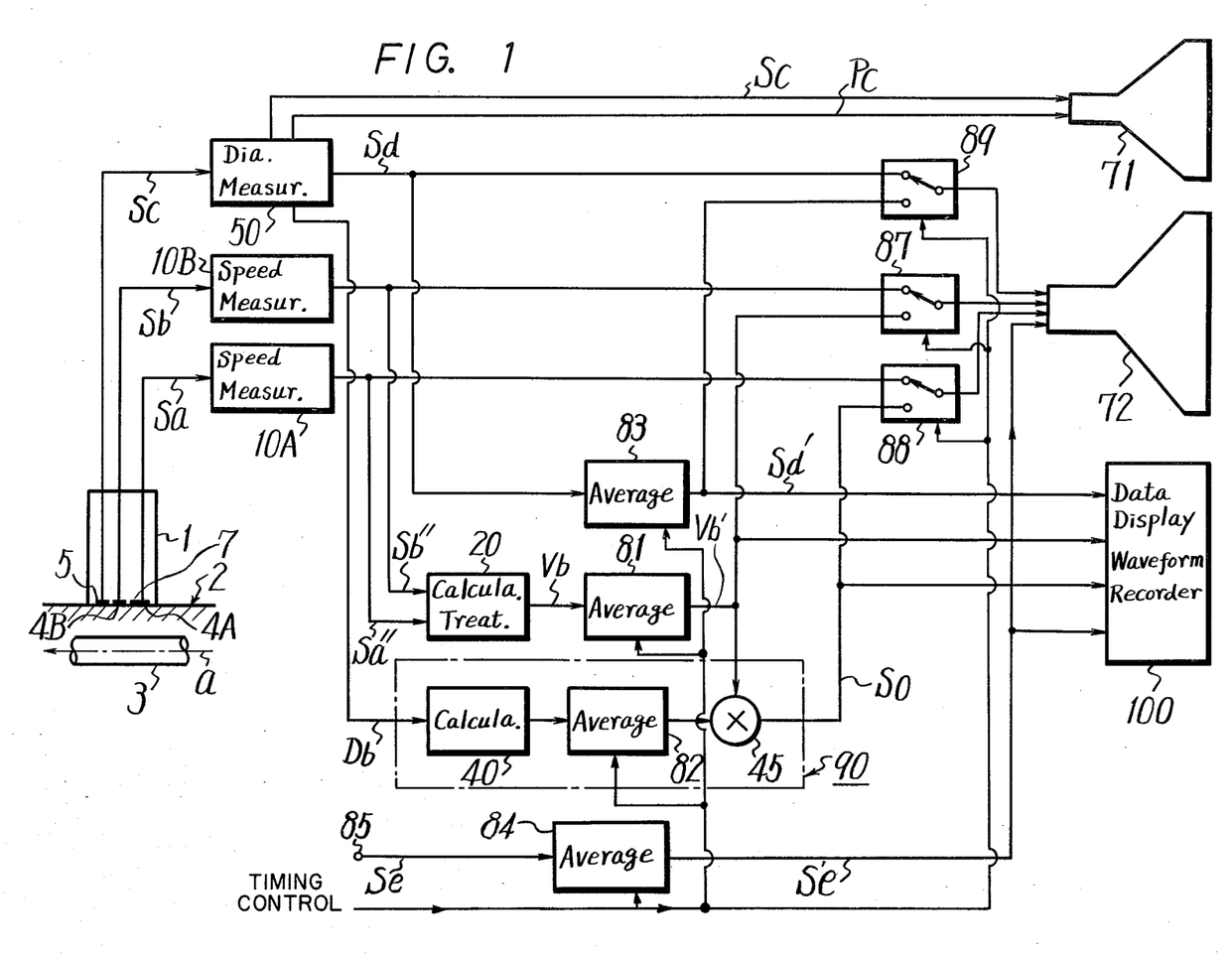
FIG. 1 is a block diagram of one embodiment of a medical measuring apparatus according to the invention.

FIG. 1 shows essential parts of a medical measuring apparatus according to the invention. The above mentioned various kinds of measured data are measured by means of ultrasonic waves without observing blood and without attacking the body. Reference numeral 1 designates an ultrasonic wave probe, 2 a body surface, and 3 a blood vessel in which the blood flows in a direction shown by an arrow a.

The ultrasonic wave probe 1 is composed of an ultrasonic continuous wave transmitting oscillating element 7, a pair of ultrasonic wave receiving oscillating elements 4A, 4B for measuring a blood flow speed and an ultrasonic pulse wave transmitting and receiving oscillating element 5 for measuring the diameter deviation of the blood vessel 1. The probe 1 will be described later in greater detail.

Reflected waves received by the pair of receiving oscillating elements 4A, 4B, that is, doppler outputs $S_a$, $S_b$ are supplied to blood flow speed measuring circuits 10A, 10B which are the same in construction, respectively, thereby obtaining a speed of blood flowing through the blood vessel 3 (blood flow speed) on the basis of the doppler outputs $S_a$, $S_b$. In addition, the reflected intermittent wave received by the transmitting and receiving oscillating element 5 is different in time from the exciting pulse in response to the blood vessel pulsatory motion. As a result, if this reflected wave is utilized, it is possible to obtain from the element 5 first, a pulse output having a width corresponding to the blood vessel diameter and second an output corresponding to the blood vessel diameter deviation. Reference numeral 50 designates a blood vessel diameter measuring circuit for obtaining from input $S_c$ the above mentioned blood vessel diameter deviation output $S_c$ and also a pulse output $P_c$ having a width corresponding to the blood vessel diameter.

The above mentioned measured data are displayed on a high speed monitor cathode ray tube 71 and low speed monitor cathode ray tube 72, respectively. That is, the output $S_c$ and pulse output $P_c$ delivered from the blood vessel diameter measuring circuit 50 are displayed on the high speed monitor cathode ray tube 71 (refer to FIGS. 5C and 5F) and the blood vessel diameter deviation output $S_d$, a pair of blood flow speed outputs $S_a''$, $S_b''$ and electrocardiogram output $S_e$ are displayed on the low speed monitor cathode ray tube 72 (refer to FIGS. 2A to 2D).

The blood flow speed outputs $S_a''$, $S_b''$ delivered from the blood flow speed measuring circuits 10A, 10B are supplied to a first calculation treating circuit 20 to obtain a blood flow speed $V_b$ which is supplied to an averaging circuit 81 to obtain an average value output $V_b''$ of the blood flow speed having five pulsations.

On the one hand, an output $D_b$ associated with the blood vessel diameter and delivered from the blood vessel diameter measuring circuit 50 is supplied to a calculation circuit 40 provided in a second calculation treating circuit 90 and for calculating the blood vessel sectional area. The output from the calculation circuit 40 is supplied through an averaging circuit 82 to a multiplier 45 to obtain an amount of blood flow $S_o$. Reference numerals 83, 84 designate averaging circuits, respectively, and 85 an input terminal of the electrocardiogram output $S_e$.

The average blood flow speed $V_b'$ delivered from the averaging circuit 81, average amount of blood flow $S_o$ delivered from the multiplier 45 and an average blood vessel diameter deviation output $S_d'$ delivered from the circuit 83 are supplied through switching circuits 87 to 89 to the cathode ray tube 72 so as to display thereon respective output wave forms. The average electrocardiogram output $S_e'$ delivered from the averaging circuit 84 is supplied to the cathode ray tube 72 so as to display thereon its output wave form (refer to FIGS. 3A to 3D). The averaging circuits 81, 82, 83 and 84 are centrally controlled in synchronism by the heartbeat as a clock source as a five pulse average so that these averaging circuits 81 to 84 respectively average the five inputs as set forth above. The control signal is also supplied to the switching circuits 87 to 89 to control the switching states thereof.

Reference numeral 100 designates a display circuit for displaying numerical values of the above mentioned measured data and a wave form recording device.

The above is the essentials of the medical measuring apparatus according to the invention. Construction and operation of the various parts thereof will now be described in succession. In the first place, the blood vessel diameter measuring circuits 50 will be described.

Figure 4:
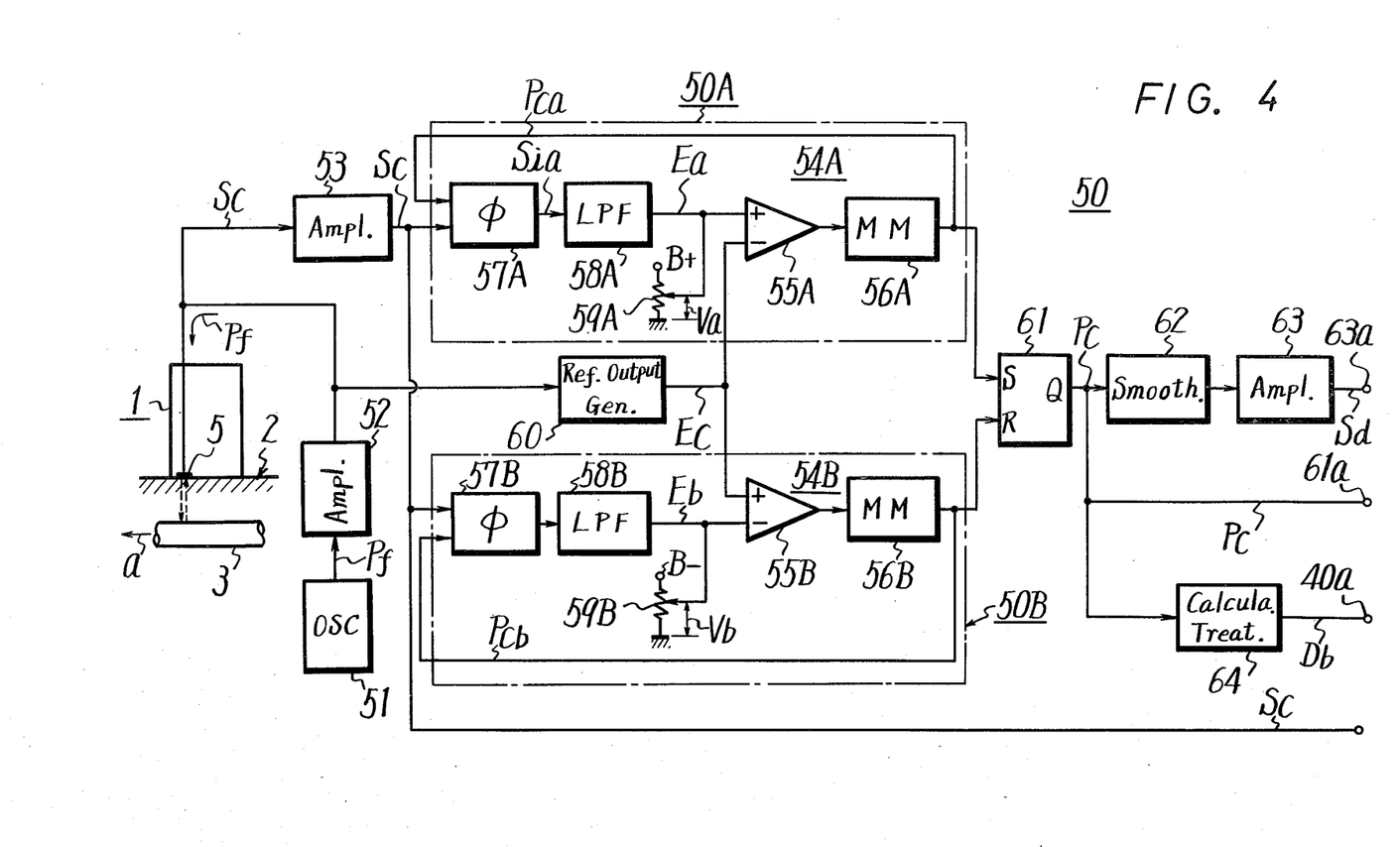
FIG. 4 is a block diagram of one embodiment of the blood vessel diameter measuring circuit shown in FIG. 1.

FIG. 4 shows one embodiment of the blood vessel diameter measuring circuit 50. Provision is made of an oscillator 51 which functions to supply an exciting pulse $P_f$, in the present embodiment a pulse output of 10 KHz, to the oscillating element 5 of the probe 1. The oscillating element 5 has an inherent oscillation frequency of 6 MHz. Reference numeral 52 designates an output amplifier.

The echo output $S_c$ (in FIG. 5C, $S_f$ shows a transmitting pulse) received by the oscillating element 5 is supplied to a wide band amplifier circuit 53 which is provided with a circuit (not shown) for trapping the doppler outputs $S_a$, $S_b$ obtained when the oscillating elements 7 (not shown) are excited.

Figures 5A, 5B, 5C:
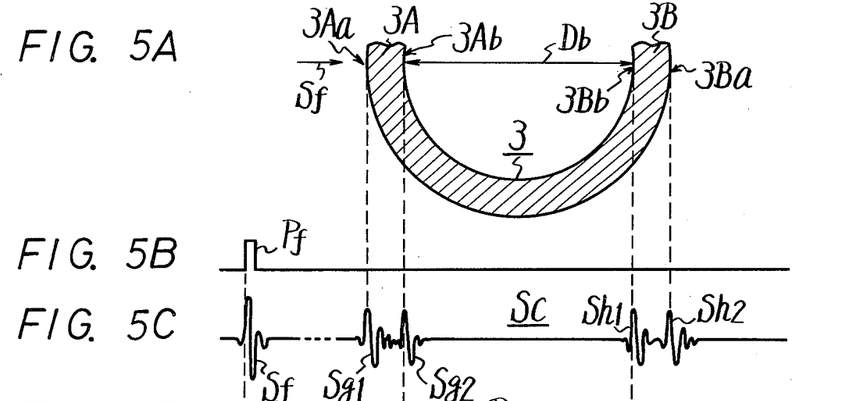
FIGS. 5A, 5B, 5C, 5D, 5E, 5F, 5G, 5H and 5I, 6A, 6B, 6C, 6D and 6E, and 7A, 7B, 7C and 7D are graphs of wave forms for illustrating the operation of the blood vessel diameter measuring circuit shown in FIG. 4.

As shown in FIG. 5C, in the echo output $S_c$, echo pulses $S_g$, $S_h$ correspond to the front wall 3A and rear wall 3B of the blood vessel 3, respectively. These echo pulses $S_g$, $S_h$ correspond to the outer diameter walls $3A_a$, $3B_a$ and inner diameter walls $3A_b$, $3B_b$, respectively. As a result, a time width between the echo pulses $S_{g2}$ and $S_{h1}$ associated with the inner diameter walls $3A_b$, $3B_b$ of the echo pulse $S_c$ corresponds to the blood vessel diameter $D_b$.

Figure 5D:
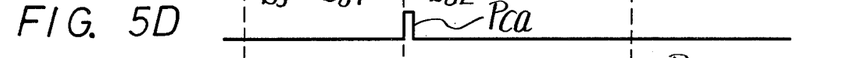

As a result, the smoothed or filtered blood vessel diameter deviation output $S_d$ is formed by gate pulses $P_{ca}$, $P_{cb}$ (FIGS. 5D and 5E) following the echo pulses $S_{g2}$ and $S_{h1}$ associated with the inner diameter walls $3A_b$, $3B_b$, respectively. In the present embodiment, the gate pulses $P_{ca}$, $P_{cb}$ are formed by a special circuit called an echo tracking circuit.

As seen in FIG. 4, the outputs $S_c$, $S_d$ and $D_b$ are used for other purposes. For example, $S_c$ is fed to the cathode ray tube 71 and displayed as a reference waveform. Signal $S_d$ is an analog signal but signal $D_b$ is a digital signal.

In FIG. 4, reference numerals 50A, 50B designate echo tracking circuits, respectively. The one circuit 50A functions to form the gate pulse $P_{ca}$, while the other circuit 50B functions to form the other gate pulse $P_{cb}$. The one echo tracking circuit 50A will now be described. Reference numeral 54A designates a delay oscillation circuit composed of a voltage comparator 55A and a monostable multivibrator 56A adapted to be triggered by the output from the voltage comparator 55A. The multi-output from the delay oscillation circuit 54A is supplied as the gate pulse $P_{ca}$ together with the echo pulse $S_c$ to a phase comparator 57A operative as a gate circuit. The gate pulse $P_{ca}$ is adjusted such that it is generated at the position of the echo pulse $S_{g2}$ of the echo pulse $S_c$ which corresponds to the inner diameter wall $3A_b$ of the front wall 3A. If the echo pulse $S_{g2}$ and the gate pulse $P_{ca}$ have a phase relation shown in FIGS. 6A and 6B, the phase comparator 57A functions to deliver an output $S_{ia}$ shown in FIG. 6C. The output $S_{ia}$ is supplied to a low-pass filter 58A which functions to smooth the output $S_{ia}$ and make its output $E_a$ zero.

Figure 7A:
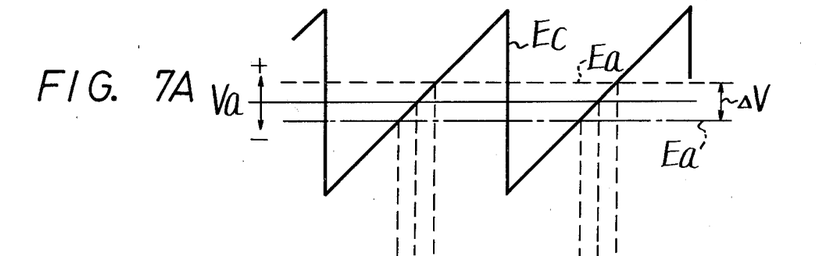

The output $E_a$ is superimposed on an offset voltage $V_a$ obtained from an offset voltage regulating variable resistor 59A and then supplied to the voltage comparator 55A. To the voltage comparator 55A is supplied a sawtooth wave-shaped reference output $E_c$ shown in FIG. 7A. Reference numeral 60 designates a circuit for forming the reference output $E_c$ and driven by the exciting pulse $P_f$. Since the exciting pulse $P_f$ has a frequency of 10 KHz, the reference output $E_c$ has a period corresponding to the exciting pulse $P_f$.

Figure 7B:
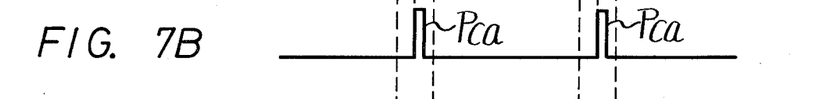

The voltage comparator 55A functions to supply a comparative output when the comparative voltage $V_a$ becomes equal to the reference output $E_c$ to the monostable multivibrator 56A so as to trigger it to produce the gate pulse $P_{ca}$ shown in FIG. 7B.

The gate pulse $P_{ca}$ has a width which is selected to be $\frac{1}{2}$ of the inherent oscillation period of the oscillating element 5.

Figure 6A:
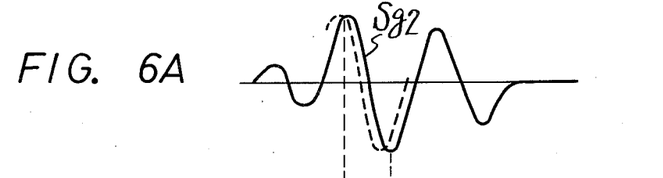
Figure 6B:
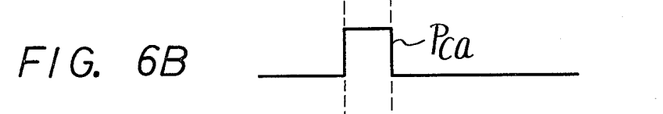
Figure 6C:
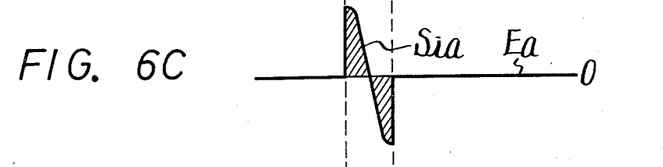
Figure 6D:
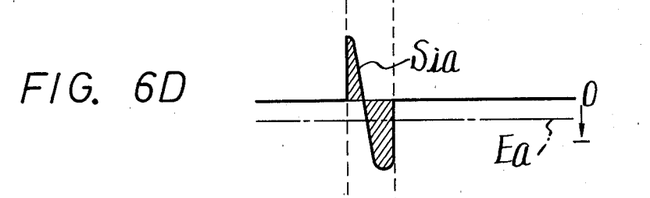
Figure 6E:
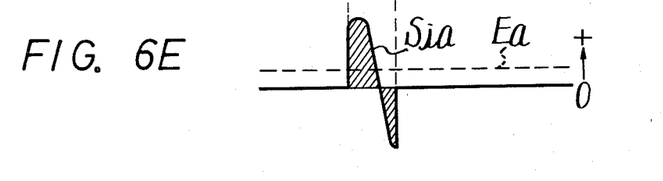
Figure 7C:
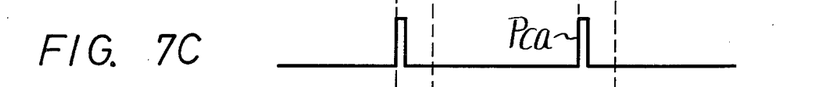
Figure 7D:
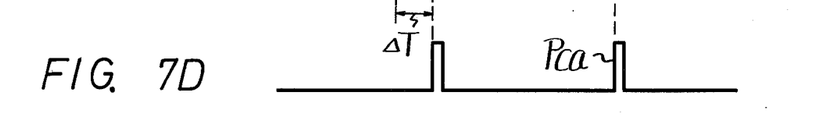

If the echo pulse $S_{g2}$ is moved to the left as shown by dotted lines in FIG. 6A with respect to the gate pulse $P_{ca}$, the gate pulse $P_{ca}$ causes the phase comparator 57A to deliver the output $S_{ia}$ shown in FIG. 6D and hence the smoothed output $E_a$ becomes negative, thereby lowering the input voltage to the voltage comparator 55A. As a result, the gate pulse $P_{ca}$ is moved to a position shown in FIG. 7C. In this case, the gate pulse $P_{ca}$ is moved to a position where the smoothed output $E_a$ becomes zero. If the echo pulse $S_{g2}$ is moved to the right contrary to the above, the output $S_{is}$ becomes one as shown in FIG. 6E and the gate pulse $P_{ca}$ is moved to the right as shown in FIG. 7D.

The blood flow in the blood vessel 3 causes the echo pulse $S_{g2}$ to change its phase, so that the deviated condition of the blood vessel wall results in the phase change of the gate pulse $P_{ca}$.

Figure 5E:
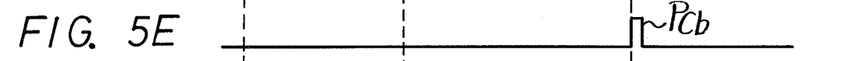

Similarly, in the other echo tracking circuit 50B, the gate pulse $P_{cb}$ corresponding to the deviation of the inner diameter wall $3B_b$ of the rear wall 3B is formed as shown in FIG. 5E. The above mentioned gate pulse $P_{ca}$ functions to set a flip-flop circuit 61. If the flip-flop circuit 61 is reset by the gate pulse $P_{cb}$, it is possible to form a pulse output $P_c$ (FIG. 5F) having a width corresponding to the blood vessel diameter $D_b$.

Figure 2A:
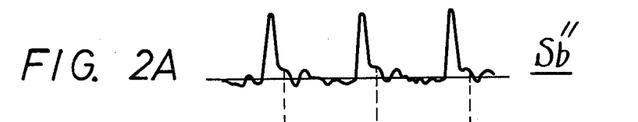
FIGS. 2A, 2B, 2C and 2D and 3A, 3B, 3C and 3D are graphs of various kinds of wave forms which can be observed by the measuring apparatus shown in FIG. 1.
Figure 2B:
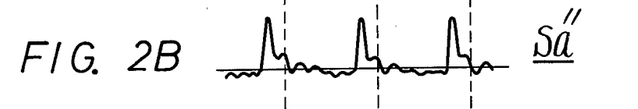
Figure 2C:
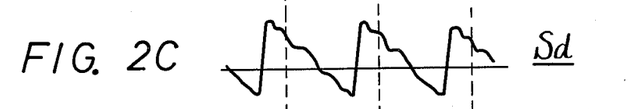
Figure 2D:
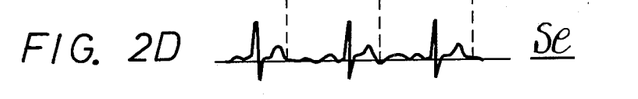
Figure 3A:
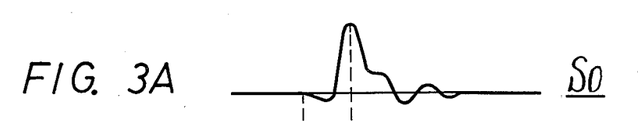
Figure 3B:
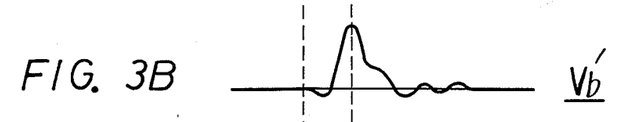
Figure 3C:
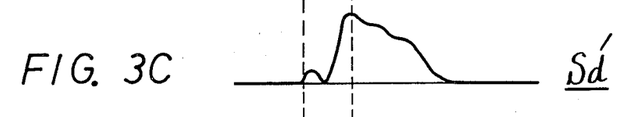
Figure 3D:
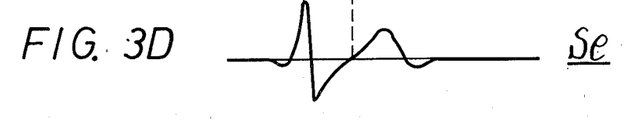
Figure 5F:
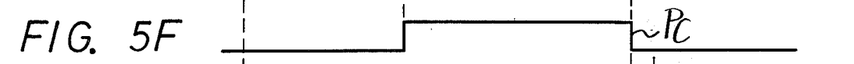
Figures 5G, 5H, 5I:
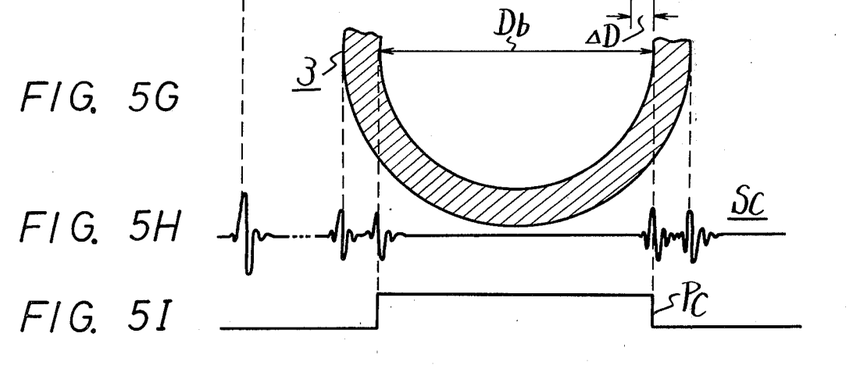

If the blood vessel 3 contracts as shown in FIG. 5A and expands as shown in FIG. 5G, such blood vessel pulsation causes the pulse output $P_c$ to change from the pulse output $P_c$ shown in FIG. 5F to the pulse output $P_c$ shown in FIG. 5I. The pulse output $P_c$ is supplied to an output terminal 61a and through a smoothing circuit 62 having a cut-off frequency of 60 Hz to a direct current amplifier circuit 63. The output from the circuit 63, that is, the smoothed or filtered blood vessel diameter deviation output $S_d$ shows that the blood flow causes the blood vessel diameter to contract and expand as shown in FIG. 2C.

The pulse $P_c$ is also supplied to a calculation treating circuit 64 so as to obtain the blood vessel diameter $D_b$ (as a digital output or analogue output).

If the variable resistors 59A, 59B are adjusted, it is possible to change the offset voltages $V_a$, $V_b$ and hence adjust the positions of the gate pulses $P_{ca}$, $P_{cb}$. As a result, the gate pulses $P_{ca}$, $P_{cb}$ can finely be adjusted with respect to the echo pulses $S_{g2}$, $S_{h1}$. Thus, it is possible to obtain the gate pulses $P_{ca}$, $P_{cb}$ which are completely coincident with the blood vessel inner walls.

A preferred ultrasonic wave probe 1 according to the invention will now be described with reference to FIGS. 8 to 12.

The blood flow speed $V_b$ is measured by means of the reflected ultrasonic wave, that is, doppler output. This doppler output becomes considerably different by the inclined angle of the probe 1 to the body surface 2, that is, the incident angle $\theta_T$ of the ultrasonic wave to the carotid artery 3.

Figure 8:
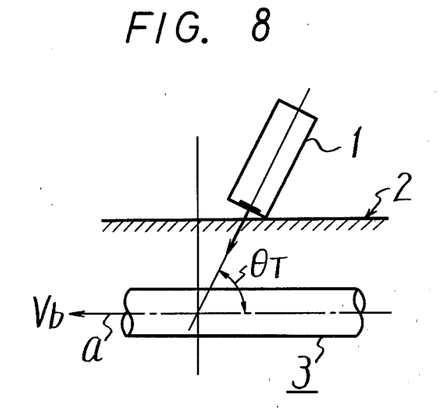
FIG. 8 is a diagrammatic view for illustrating an ultrasonic wave probe.

It is impossible to always maintain the incident angle $\theta_T$ at a constant angle during measurement of the blood flow speed, so that it is impossible to precisely measure the blood flow speed by means of the probe 1 shown in FIG. 8.

In order to eliminate the measurement error, the blood flow speed may be measured by means of a pair of probes and may use the reflected waves obtained from these probes. The reasons why the measurement error can be eliminated will be described later.

Figure 9:
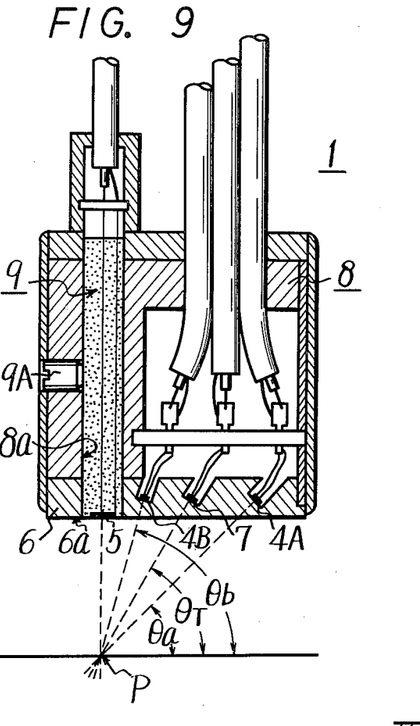
FIG. 9 is a longitudinal sectional view of a preferred embodiment of an ultrasonic wave probe according to the invention.

The ultrasonic wave probe 1 shown in FIG. 9 makes use of at least three ultrasonic wave oscillating elements for the purpose of measuring the blood flow speed. (In principle, provision must be made of two ultrasonic wave transmitting oscillating elements and two ultrasonic wave reciving oscillating elements.)

The embodiment shown in FIG. 9 makes use of three oscillating elements. Reference numeral 6 designates an oscillating element supporting plate. The supporting plate 6 is provided at its given position with an ultrasonic wave transmitting oscillating element 7 inclined at a given incident angle with respect to the plane 6a of the supporting plate 6 for the purpose of measuring the blood flow speed, and provided in front and rear of the ultrasonic wave transmitting oscillating element 7 with a pair of ultrasonic continuous wave receiving oscillating elements 4A, 4B which are inclined at angles $\theta_a$, $\theta_b$ adapted to receive the reflected waves from a point P, respectively. Practical examples of the angles $\theta_a$, $\theta_b$ will be described later. These oscillating elements 7, 4A, 4B are aligned with each other as shown in FIG. 10.

Figure 10:
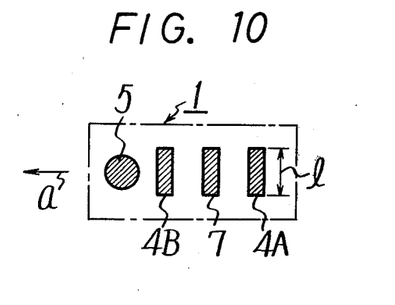
FIG. 10 is its base view.

These oscillating elements 7, 4A, 4B are rectangular in section as shown in FIG. 10 and each has a length l determined on the basis of the blood vessel diameter to be measured. Since the blood vessel diameter $D_b$ is on the order of at most 7 to 10 mm, it is preferable to select the length l to the order of 10 mm. Each of the oscillating elements 7, 4A, 4B is composed of a ceramic oscillating element having an inherent oscillation frequency of 5 MHz.

The use of the ultrasonic wave transmitting oscillating element 7 interposed between the pair of ultrasonic wave receiving oscillating elements 4A, 4B ensures an omission of an independent ultrasonic wave transmitting oscillating element for each of the ultrasonic wave receiving oscillating elements 4A, 4B. In addition, the presence of only one ultrasonic wave transmitting oscillating element 7 causes the ultrasonic wave receiving oscillating elements 4A, 4B to receive the reflected wave from the point P without being deviated therefrom.

The blood vessel diameter deviation measuring oscillating element 5 is arranged at one side of the ultrasonic wave receiving oscillating element 4B. In practice, the oscillating element 5 is aligned with the other oscillating elements 7, 4A, 4B and arranged in front of the oscillating element 4B such that the ultrasonic pulse wave incident angle thereof is at right angles to the blood vessel 3. In addition, the oscillating element 5 is arranged such that the ultrasonic wave passing therethrough strikes on the same point P as the ultrasonic wave passing through the oscillating element 7.

As shown in FIG. 9, the supporting plate 6 and a reinforcing member 8 are provided with a bore 8a extending therethrough and the bore 8a is filled with a packing material 9. The oscillating element 5 is firmly secured to front end of the packing material 9. Reference numeral 9A designates a screw for securing the packing material 9 to the reinforcing member 8.

The oscillating element 5 is formed of barium titanate and functions to transmit and receive the ultrasonic wave. The oscillating element 5 is intermittently excited by a pulse $P_f$ of 10 KHz delivered from the oscillator 51.

Figure 13:
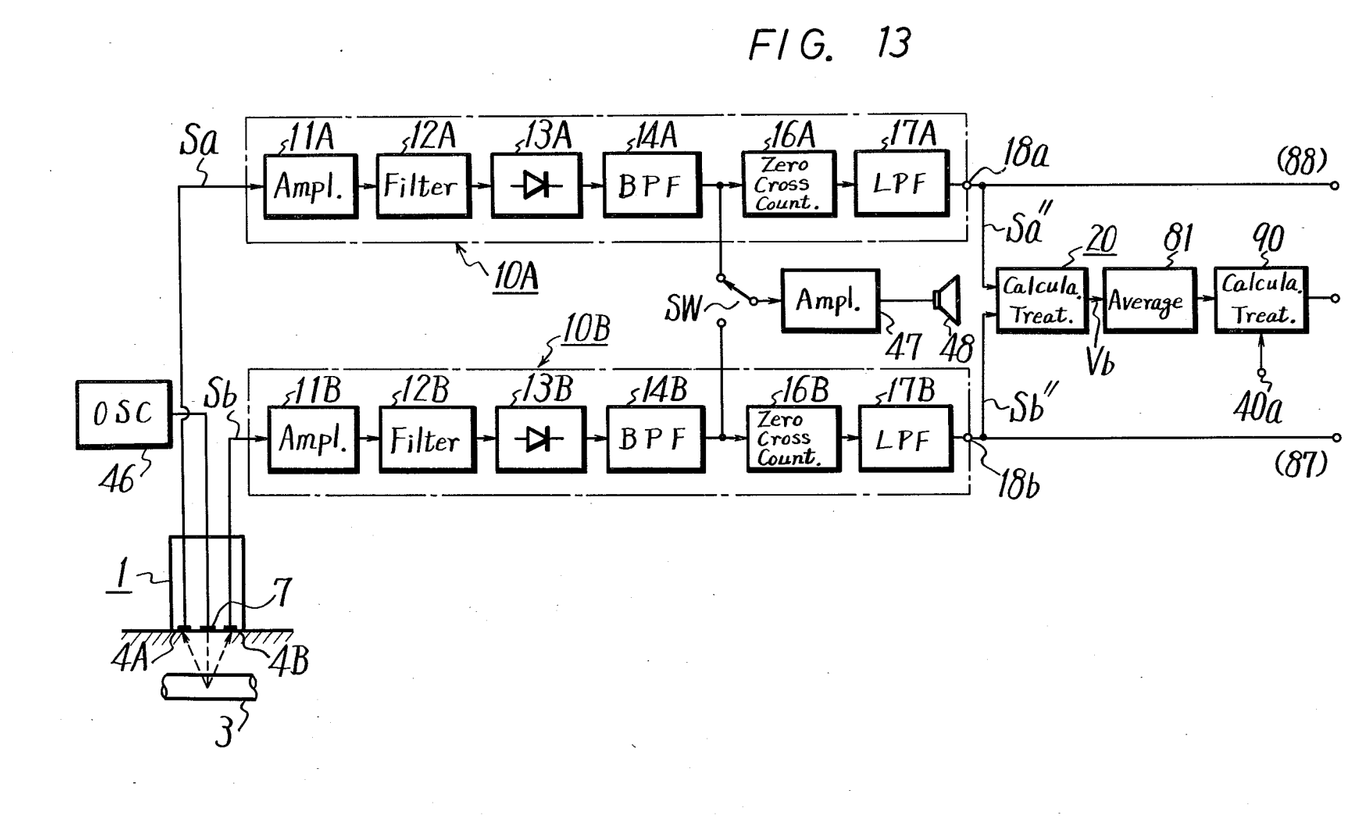
FIG. 13 is a block diagram of one embodiment of a circuit for measuring an amount of blood flow according to the invention.

While the continuous wave emitted from element 7 and the reflected wave are also received by element 5, the existence of a frequency difference of 1 MHz between those emitted from element 5 and 7 enables the easy removal of any unwanted waves on the receivers through the use, for example, of the filters 12A and 12B shown in FIG. 13.

The blood flow speed $V_b$ may be obtained in the following manner by means of the ultrasonic wave probe 1 constructed as above described.

Let it be assumed that the oscillating element 7 is inclined at an angle $\theta_T$ to the blood vessel 3, that the oscillating element 4A is inclined at an angle $\theta_a$ to the blood vessel 3 and that the oscillating element 4B is inclined at an angle $\theta_b$ to the blood vessel 3. If the blood flow is measured under the condition that $\theta_b - \theta_a = \theta$ is always held at a given angle, it is always possible to obtain a constant measured output irrespective of the inclined angle of the ultrasonic wave probe 1 with respect to the body surface 2.

The reasons for the above will be described with reference to FIG. 12. It is known that the reflected wave of the ultrasonic wave emitted from the oscillating element 7, that is, the doppler output is proportional to the flow speed $V_b$ of the blood flowing through the carotid artery 3 and to the cosine of the ultrasonic wave receiving angle.

That is, the doppler outputs $S_a$, $S_b$ received by the oscillating elements 4A, 4B are given by the following formulas (1) and (2), respectively.

$$S_a = kV_b \cos\left(\frac{\theta_T + \theta_b}{2}\right) \quad (1)$$

$$S_b = kV_b \cos\left(\frac{\theta_T + \theta_a}{2}\right) \quad (2)$$

where $$k = 2f_s/C \ldots \quad (3)$$

Figure 11:
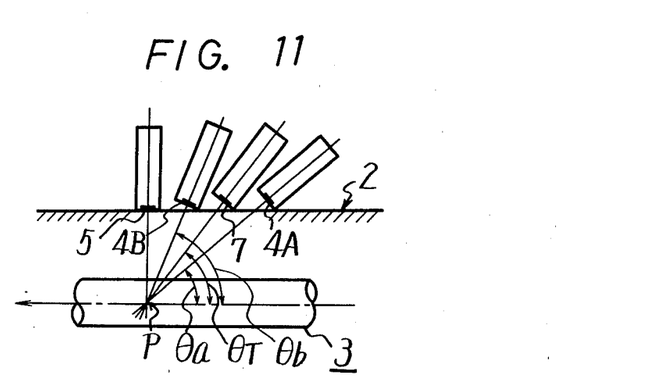
FIGS. 11 and 12 are diagrammatic views illustrating the operation of the ultrasonic wave probe, respectively.
Figure 12:
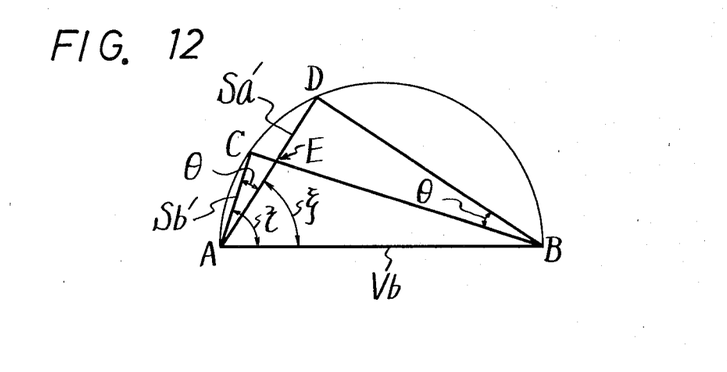

$f_s$ is an inherent oscillation frequency of the oscillating element 7.
C is a transmission speed.
Now, let it be assumed that $$\left. \begin{array}{l} \dfrac{\theta_T + \theta_b}{2} = \eta \\ \dfrac{\theta_T + \theta_a}{2} = \xi \end{array} \right\} \quad \ldots (4)$$

then, if points C and D are located on the periphery of a circle having a diameter of $\overline{AB}$ as shown in FIG. 12, the doppler output $S_a'$ represented by a segment $\overline{AD}$ and the doppler output $S_b'$ represented by a segment $\overline{AC}$ are given by $$\left. \begin{array}{l} S'_a = \dfrac{S_a}{k} \\ S'_b = \dfrac{S_b}{k} \end{array} \right\} \quad \ldots (5)$$

because the ultrasonic wave receiving angles shown in FIG. 11 are different from those shown in FIG. 12.
In FIG. 12, $V_b$ is given by $$V_b = \sqrt{\overline{AD}^2 + \overline{DB}^2} \quad (6)$$

Let it be assumed that $\eta - \xi = \theta_b - \theta_a = \theta$, $\overline{DB}$ is given by $$\overline{DB} = \dfrac{\overline{DE}}{\tan \theta} = \dfrac{S'_a - S'_b}{\cos \theta \cdot \tan \theta} \quad (7)$$

$$= S'_a \cot \theta - \dfrac{S'_b}{\sin \theta}$$

Accordingly, the blood flow speed $V_b$ defined by the formula (6) is given by $$V_b = \sqrt{S'_a{}^2 + \left( S'_a \cot \theta - \dfrac{S'_b}{\sin \theta} \right)^2} \quad (8)$$

$$= \dfrac{S_a}{k} \sqrt{1 + \left( \cot \theta - \dfrac{S_b}{S_a} \cdot \dfrac{1}{\sin \theta} \right)^2}$$

As seen from the formula (8), the blood flow speed $V_b$ is a function of the mechanical angle $\theta$ defined by $\theta_a$, $\theta_b$, but is not dependent on the inclined angle of the probe 1 to the body surface. That is, the blood flow speed $V_b$ is not dependent on the angle.

As a result, it is possible to measure the blood flow speed irrespective of the change of the inclined angle of the probe 1 with respect to the body surface 2.

The angle $\theta$ is not limited to a specially defined value. In the present embodiment, $\theta$ is selected to be 20°. As described above, the measurement error becomes the smallest when $\theta_T = 60°$, and as a result, the ultrasonic wave incident angle $\theta_T$ of the oscillating element 7 is selected to about 60°. In the present embodiment, the selection is made as $\theta_T = 65°$, $\theta_a = 55°$ and $\theta_b = 75°$.

FIG. 13 shows a circuit for measuring the amount of blood flow. In FIG. 13, reference numeral 46 designates an ultrasonic wave oscillator, which supplies a continuous signal to the oscillating element 7. The reflected waves, that is, the doppler outputs $S_a$, $S_b$ are supplied from the element 4A and 4B; and to measuring circuits 10A, 10B, respectively. These measuring circuits 10A, 10B are used for the purpose of obtaining blood flow wave forms and are substantially the same in circuit construction. As a result, the measuring circuit 10A associated with the doppler output $S_a$ will be described.

The doppler output $S_a$ is supplied to an amplifier 11A and then supplied through a filter 12A, which is composed of quartz and functions to remove the output produced by the reverse flow of the blood, to a detector circuit 13A. The doppler output is subjected to envelope detection and then supplied to a band-pass filter 14A. The lower limit of the filter 14A is determined for the purpose of removing the doppler signal produced when the blood vessel contracts and expands, and the upper limit of the filter 14A is determined by taking S/N ratio into consideration. In the present embodiment, the band-pass filter 14A is constructed such that frequencies 80 Hz to 7 KHz may pass therethrough.

The output from the band-pass filter 14A may be supplied through a switch SW and amplifier 47 to a speaker 48. The speaker 48 serves to listen for the doppler output, that is, the blood flow sound.

The output from the band-pass filter 14A is also supplied through a zero-cross counter 16A to a low-pass filter 17A from which is delivered the final output $S_a''$ of the measuring circuit 10A.

The output $S_a''$ is supplied through the switch circuit 88 to the cathode ray tube 72 (refer to FIG. 1).

The other blood flow speed measuring circuit 10B also functions to produce an output $S_b''$ associated with the doppler output $S_b$ delivered from the oscillating element 4B. These outputs $S_a''$, $S_b''$ are supplied to a first calculation treating circuit 20 for the purpose of effecting the calculation treatment shown by the formula (8).

Figure 14:
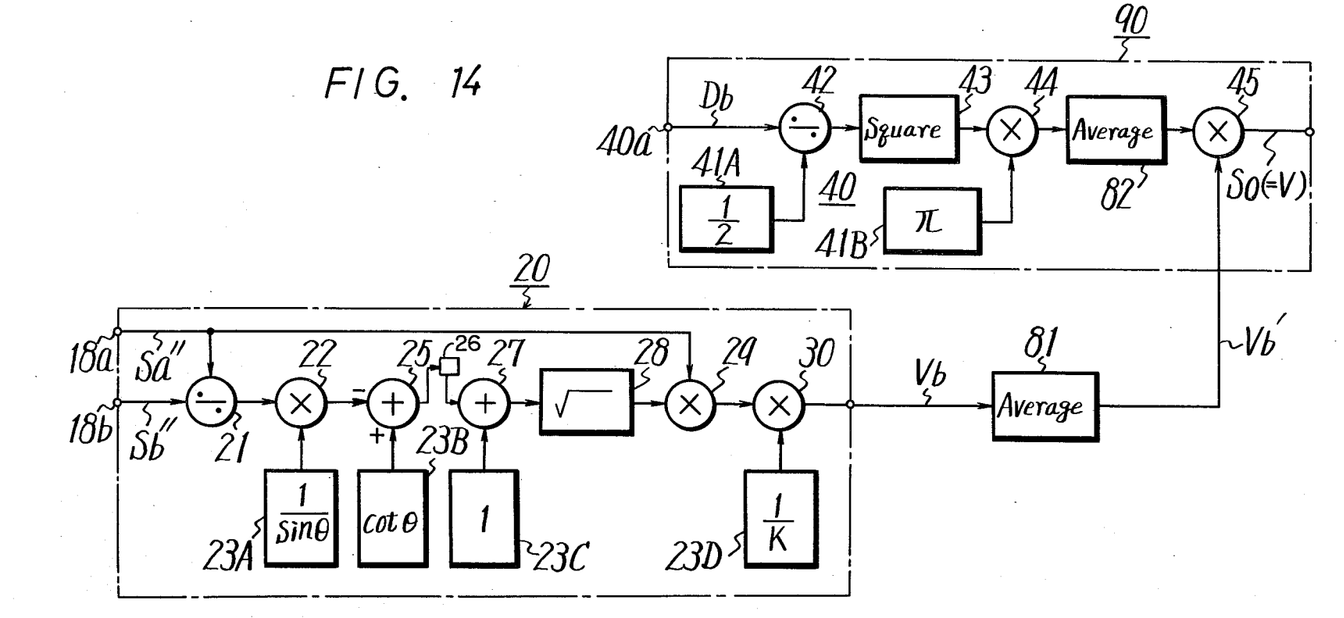
FIG. 14 is a block diagram of one embodiment of a first calculation treating circuit and second calculation treating circuit according to the invention.

FIG. 14 shows the first calculation treating circuit 20 constructed so as to obtain the blood flow speed $V_b$ from the formula (8).

The outputs $S_a''$, $S_b''$ are supplied to a divider circuit 21 so as to effect $S_b''/S_a''$ treatment and then to a multiplier circuit 22.

To the multiplier circuit 22 is supplied an output 1/sin $\theta$ from a constant circuit 23A. The output from the multiplier circuit 22 is supplied to an adder 25 to which is also supplied an output cot $\theta$ from a constant circuit 23B. The adder 25 functions to effect the calculation treatment of (cot $\theta - (S_b''/S_a'') \times 1/\sin \theta$).

The output from the adder 25 is supplied through a square circuit 26 to an adder 27 to which is also supplied an output 1 (one), which is included in the square root $\sqrt{\phantom{x}}$ shown in the formula (8), from a constant circuit 23C. The adder 27 functions to effect the calculation in the square root of the formula (8). The output from the adder 27 is supplied to a square root circuit 28 whose output together with the above mentioned output $S_a''$ are supplied to a multiplier 29. The output from the multiplier 29 is supplied to a multiplier 30 to which is also supplied an output 1/k from a constant circuit 23D. The multiplier 30 functions to effect all calculation given by the formula (8). As a result, from the output terminal of the multiplier 30 is delivered the blood flow speed $V_b$ given by the formula (8).

The amount of blood flow is obtained from the product of the unit sectional area of the carotid artery and the blood flow speed $V_b$.

For this purpose, provision is made of a second calculation treating circuit 90 in the following stage of the first calculation treating circuit 20 as shown in FIG. 13. The second calculation treating circuit 90 functions to effect the calculation treatment for the amount of blood flow.

The second calculation treating circuit 90 will be described with reference to FIG. 14. The blood vessel diameter $D_b$ of the carotid artery is given by the output from the calculation treating circuit 64 shown in FIG. 4, so that the amount of blood flow can simply be calculated by means of the output $D_b$. That is, the amount of blood flow $S_o$ (volume is V) is given by $$V = V_b' \cdot \pi \cdot (D_b/2)^2 \ldots \quad (9)$$

where $V_b'$ is an average value output of the blood flow speed $V_b$.

The calculation treatment of the formula (9) will now be described. Reference numeral 41A designates a constant circuit and 42 a divider circuit. To the input terminal 40a of the divider circuit 42 is supplied the output associated with the above mentioned blood vessel diameter $D_b$. The divider circuit 42 functions to effect the calculation of $D_b/2$. The output from the divider 42 is supplied to a square circuit 43 and then to a multiplier 44 which functions to multiply a constant $\pi$ delivered from a constant circuit 41B. The output from the multiplier 44 is supplied through an averaging circuit 82 to a multiplier 45 together with the average blood flow speed $V_b'$ delivered from the first calculation treating circuit 20.

In this way, it is possible to obtain the final amount of blood flow V and know the absolute amount $S_o$ of blood flow necessary for the blood vessel properties as described in the preamble of the specification.

As stated hereinbefore, the invention is capable of observing several of the blood vessel properties of the carotid artery through the wave forms and hence precisely predicting the cerebral blood vessel defects. In this case, the measured data of the amount of blood flow is one property finally required. But, the use of such measured data only blood flow could not make clear the relation between the blood vessel diameter $D_b$ and the blood flow speed $V_b$, and as a result, it would be impossible to precisely predict the cerebral blood vessel defects. The present invention, however, is capable of observing the intermediate measured data for obtaining the amount of blood flow, particularly, the blood vessel diameter deviation output $S_d$ and the pulse output $P_c$ corresponding to the blood vessel diameter through the wave forms and hence effectively knowing all the blood vessel properties.

In the above described embodiment, the calculation treating circuits 20 and 90 have been shown as analogue circuits, but these circuits 20 and 90 may be composed of digital circuits.

It will be apparent that many modifications and variations may be effected without departing from the scope of the novel concepts of this invention.

We claim as our invention:

1. A medical measuring apparatus comprising: a probe adapted to be held in contact with a body surface of a patient adjacent a blood vessel, said probe having mounted therein to be in alignment with the blood vessel (a) an ultrasonic transmitting oscillating element inclined to be at an acute angle to the blood vessel (b), a pair of ultrasonic wave receiving oscillating elements arranged in front and rear of said transmitting oscillating element and inclined to be at acute angles to the blood vessel and (c), an ultrasonic wave transmitting and receiving oscillating element located at one side of one of said pair of receiving oscillating elements to be at right angles to said blood vessel, each of said ultrasonic transmitting oscillating element and said pair of ultrasonic wave receiving elements having a length at least equal to the diameter of said blood vessel;

first means for continuously driving said ultrasonic wave transmitting oscillating element to emit a continuous ultrasonic wave;

second means for intermittently driving said ultrasonic wave transmitting and receiving oscillating element to emit a pulsating ultrasonic wave;

said pair of receiving elements receiving a continuous ultrasonic wave reflected from the blood flow, said transmitting and receiving oscillating element receiving a pulsating ultrasonic wave reflected from the blood vessel;

third means for receiving an output from said pair of receiving elements and generating a signal representing blood flow speed;

fourth means for receiving an output from said transmitting and receiving oscillating element and producing a signal output representing blood vessel diameter deviation and a pulse output having a width corresponding to the blood vessel diameter;

fifth means for producing a signal representing blood flow amount from the signals delivered from said third and fourth means;

sixth means for controlling said third and fourth means in response to an electrocardiogram output of the patient;

a first cathode ray tube for displaying the signals representing the blood flow speed, blood flow amount and blood vessel diameter deviation; and a second cathode ray tube for displaying the signal representing the blood vessel diameter deviation output and also displaying the pulse output having the width corresponding to the blood vessel diameter.

2. The apparatus as claimed in claim 1, wherein said third means includes a blood flow speed measuring circuit, a first calculation treating circuit and a first averaging circuit, and said fourth means includes a blood vessel diameter measuring circuit, a calculation circuit and a second averaging circuit.

3. The apparatus according to claim 2, wherein said blood vessel diameter measuring circuit comprises first and second echo tracking circuits, each being composed of a phase comparator having two input terminals one of which is connected to said ultrasonic wave transmitting and receiving oscillating element, the other input terminal of which receives the pulse output, a low-pass filter connected to said phase comparator having two input terminals one of which is connected to said low-pass filter and to an offset voltage regulating variable resistor and the other input terminal of which is connected to a reference output forming circuit, and a monostablemultivibrator connected to said voltage comparator, and further comprises a flip-flop circuit connected to said first and second echo tracking circuits and directly delivering said pulse output having the width corresponding to the blood vessel diameter to said first cathode ray tube, delivering said blood vessel diameter deviation output through a smoothing circuit and an amplifier to said second cathode ray tube and delivering said blood vessel diameter output through a calculation treating circuit to said second calculation treating circuit.

4. The apparatus according to claim 2 wherein said blood flow speed measuring circuit comprises an amplifier connected to said ultrasonic wave receiving oscillating element, a filter, a detector circuit, a bandpass filter, a zero-cross counter and a low-pass filter, all these circuit elements being connected in series with each other.

5. The apparatus according to claim 2 wherein said first calculation treating circuit comprises a divider connected to both said blood flow speed measuring circuits, a first multiplier connected to said divider, a $1/\sin \theta$ supplying constant circuit connected to said first multiplier, a first adder connected to said multiplier, a $\cos \theta$ supplying constant circuit connected to said first adder, a square circuit connected to said first adder, a second adder connected to said square circuit, a constant circuit connected to said second adder, a square root circuit connected to said second adder, a second multiplier connected to said square root circuit, a third multiplier connected to said second multiplier, and a $1/k$ supplying constant circuit connected to said third multiplier.

6. The apparatus according to claim 2 wherein said second calculation treating circuit comprises a divider connected to said blood vessel diameter measuring circuit, a ½ supplying constant circuit connected to said divider, a square circuit connected to said divider, a first multiplier connected to said square circuit, a $\pi$ supplying constant circuit connected to said first multiplier, said second averaging circuit connected to said first multiplier, and a second multiplier connected to said second averaging circuit and through said first averaging circuit to said first calculation treating circuit.

* * * * *